(12) United States Patent
Knell et al.

(10) Patent No.: US 6,320,053 B1
(45) Date of Patent: Nov. 20, 2001

(54) PREPARATION OF HETEROARYLCARBOXAMIDES

(75) Inventors: Marcus Knell; Monika Brink, both of Ingelheim; Jan Hendrik Wevers, Maniz-Kastel; Willi Heinz, Mainz, all of (DE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/564,273

(22) Filed: May 4, 2000

Related U.S. Application Data

(62) Division of application No. 09/118,580, filed on Jul. 17, 1998, now Pat. No. 6,087,506.
(60) Provisional application No. 60/066,620, filed on Nov. 26, 1997.

(30) Foreign Application Priority Data

Aug. 19, 1997 (EP) .................................................... 9714250

(51) Int. Cl.[7] ................................................. C07D 213/02
(52) U.S. Cl. ...................... 546/298; 546/291; 546/323; 546/326; 546/327
(58) Field of Search ..................... 546/291, 298, 546/232, 326, 327

(56) References Cited

U.S. PATENT DOCUMENTS

| 3,317,549 | * | 5/1967 | Johnston | 546/286 |
| 4,110,373 | * | 8/1978 | Day | 260/543 |
| 4,212,819 | * | 7/1980 | Day | 260/543 |

FOREIGN PATENT DOCUMENTS

| 0 646 566 | * | 11/1997 | (EP) . |
| 0 447 004 | * | 1/1998 | (EP) . |

* cited by examiner

Primary Examiner—Zinna Northington Davis
(74) Attorney, Agent, or Firm—Barbara V. Maurer

(57) ABSTRACT

The invention relates to a process for the preparation of hetero)aryloxyheteroarylcarboxylic amide or ester of formula VI

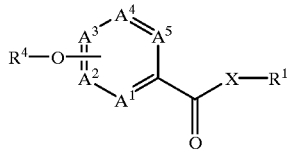

VI wherein $A^1, A^2, A^3, A^4, A^5$ Hal, X, $R^1$, and $R^4$ are defined within, which process comprises preparing the heteroarylcarboxylic amide or ester of formula I or a salt thereof,

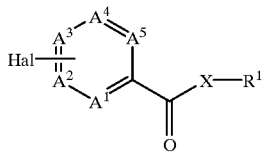

I from a trichoromethyl-heteroaromatic compound of formula II

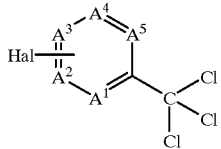

II and reacting the compound of formula I with an aromatic or heteroaromatic hydroxyl compound of formula VII, $R^4$—OH         VII optionally in the presence of a base.

12 Claims, No Drawings

PREPARATION OF HETEROARYLCARBOXAMIDES

This is a divisional application of Ser. No. 09/118,580 filed Jul. 17, 1998, now U.S. Pat. No. 6,087,506 which claims the benefit of priority to provisional application No. 60/066,620 filed Nov. 26, 1997. The entire disclosure of which is hereby incorporated by reference.

This Application claims priority of EP 97 114250.0, filed Aug. 19, 1997 and provisional U.S. Ser. No. 60/066620, filed Nov. 26, 1997.

BACKGROUND OF THE INVENTION

Heteroarylcarboxylic amides and esters are suitable intermediates for the preparation of a broad variety of compounds which are useful as agrochemicals or pharmaceuticals. In particular, they are key intermediates in the preparation of herbicidal aryloxyheteroarylcarboxamides which are described, for example, in EP 0 447 004 A or WO 94/27974.

European patent application EP 0 646 566 A suggests the hydrolyzation of trichloromethyl heteroarenes with water in the presence of chlorinated hydrocarbons and a Lewis acid, followed by reaction of the resulting heteroarylcarbonyl chloride with an amine. However, this process causes problems with respect to the rate and the exact equimolar addition of water. Any excess of water will cause hydrolysis of the desired acid chloride compound and therefore reduce the yields. Moreover, the use of chlorinated hydrocarbons is undesirable due to environmental problems, and a large amount of solvent is required. Furthermore, a very long (24 hour) reaction time using water/1,2-dichloroethane is necessary.

It is also known that pyridinecarboxylic acids are reparable by the hydrolysis of the corresponding (trichloromethyl)pyridine compound in a strong acid such as sulfuric acid or nitric acid (U.S. Pat. No. 3,317,549). German patent application DE 28 40 924 discloses a process in which benzotrihalides are treated with concentrated or fumic sulfuric acid. This process yields mixtures of benzoylhalides and halosulfonylbenzoylhalides.

SUMMARY OF THE INVENTION

The present invention provides an effective and efficient process for the preparation of heteroarylcarboxylic amides and esters of formula I

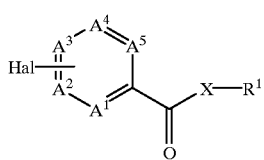

wherein
one or two of the groups $A^1$, $A^2$, $A^3$, $A^4$ and $A^5$ represent a nitrogen atom and the other groups each independently represent $CR^3$,
Hal represents a halogen atom,
X represents oxygen or $NR^2$,
$R^1$ represents an optionally substituted alkyl, aryl, heteroaryl or cycloalkyl group,
$R^2$ represents a hydrogen atom or an alkyl group, or
$R^1$ and $R^2$ together with the interjacent ring form a heterocyclic group, and $R^3$ each independently represent a hydrogen atom or an alkyl group, which comprises the following steps:

a) heating a mixture consisting essentially of a heteroaryltrichloromethane compound of formula II,

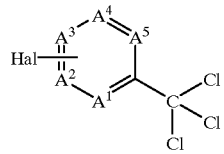

wherein
Hal and $A^1$ through $A^5$ are as hereinbefore defined,
and 1.0 to 1.5 equivalents of concentrated sulfuric acid, b) reacting the intermediate product obtained in step (a) with an amine or alcohol of formula III, $$HXR^1 \qquad III$$

wherein X and $R^1$ are as hereinbefore defined, optionally in the presence of a diluent and/or a base.

It is, therefore, an object of the present invention to provide an efficient new process for the preparation of heteroarylcarboxylic amides and esters in high yield and purity.

Another aspect of the present invention is a process for the preparation of a (hetero)aryloxyheteroaryl-carboxylic amide or ester of formula VI

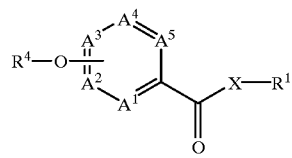

wherein $A^1$ through $A^5$, $R^1$ and X are as hereinbefore defined, and $R^4$ represents an optionally substituted aryl or heteroaryl group, wherein the heteroarylcarboxylic amide or ester of formula I or a salt thereof, is prepared from a trichoromethyl-heteroaromatic compound of formula II and is reacted with an aromatic or heteroaromatic hydroxyl compound of formula VII, $$R^4-OH \qquad VII$$

wherein $R^4$ is as hereinbefore defined, optionally in the presence of a base.

Other objects and advantages of the present invention will be apparent to those skilled in the art from the following description and the appended claims.

DETAILED DESCRIPTION OF THE INVENTION

The heteroaryltrichloromethane compounds of formula II include pyridines, pyrimidines and pyrazines which are substituted by one trichloromethyl group, one halogen atom and optionally by one to three alkyl groups. The pyridines of formula IIa are preferred:

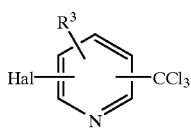

(IIa)

wherein $R^3$ represents a hydrogen atom or an alkyl group and Hal represents a halogen atom, preferably a chloro atom; in particular those of formula IIa1:

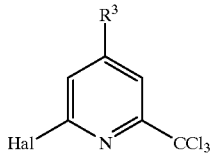

(IIa1)

wherein Hal and $R^3$ are as hereinbefore defined; most preferred is nitrapyrin (NP), a compound of formula IIa1, in which Hal is Cl and $R^3$ is H.

In general terms, unless otherwise stated herein, the term "optionally substituted alkyl, aryl, heteroaryl or cycloalkyl group" as used herein with respect to $R^1$ or $R^4$ refers to a alkyl, phenyl, pyridine, pyrimidine or a $C_{3-8}$ cycloalkyl group optionally substituted by one or more halogen atoms, nitro, cyano, alkyl, preferably $C_{1-6}$ alkyl, alkoxy, preferably $C_{1-6}$ alkoxy, or haloalkyl, preferably $C_{1-6}$ haloalkyl groups.

As a rule, aromatic or heteroaromatic groups are preferred, which are substituted by at least one electron-withdrawing group, in particular, by one or more halogen atoms, nitro, cyano or haloalkyl groups.

In general terms, unless otherwise stated herein, the term "alkyl" or "haloalkyl" as used herein with respect to a radical or moiety refers to a straight or branched chain radical or moiety. As a rule, such radicals have up to 10, in particular up to 6 carbon atoms. Typically, an alkyl or haloalkyl moiety has from 1 to 6 carbon atoms, preferably from 1 to 3 carbon atoms. A preferred alkyl moiety is the methyl, ethyl or isopropyl group.

If $R^1$ and $R^2$ together with the interjacent ring form a heterocyclic group, it is preferably a heterocyclic group having 5 to 8 ring atoms and preferably a piperidin-1-yl or a morpholin-1-yl group.

Preferred haloalkyl groups are poly- or perhalogenated alkyl groups of formula —$(CX_2)_n$—Y, in which n is an integer of 1 to 10, preferably, 1 to 6, in particular, 1 to 3, X represents fluorine or chlorine and Y is hydrogen or X. A preferred perhalognated alkyl moiety is a pentafluoroethyl, or especially a difluoro- or a trifluoromethyl group.

Optionally substituted moieties may be unsubstituted or have from one up to the maximal possible number of substituents. Typically, 0 to 2 substituents are present.

Further preferred embodiments of the process according to the present invention are a process wherein:

the concentrated sulfuric acid is added slowly to compound of formula II at temperatures between 1 about 110 and 150° C. (step a);

the mixture of the heteroaryltrichloromethane compound of formula II and 1.0 to 1.5 equivalents of concentrated sulfuric acid is kept at temperatures between about 110 and 150° C. (step a);

the intermediate product formed in step a) is added to the amine or alcohol of formula III in melted form (step b);

the heteroaryltrichloromethane compound is treated with concentrated sulfuric acid containing less than 3 wt % of water;

the intermediate product formed in step a) is treated with a straight-chained or branched aliphatic alcohol having 1 to 6 carbon atoms (step b), in particular with ethanol or isopropanol;

in the event that the intermediate of step a) has not been treated with an alcohol, the reaction of step b) is carried out in the presence of a tertiary amine as a base and an aromatic hydrocarbon as a diluent;

in the event that the intermediate of step a) has been treated with an alcohol (step b), the reaction with the amine of formula III is carried out in the presence of a metal alkoxide as a base and an aromatic hydrocarbon as a diluent;

the intermediate product formed in step a) comprises a compound of formula IV and/or V

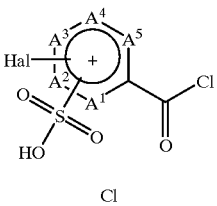

IV

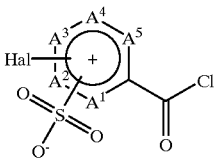

V or a structure isomeric form thereof; or preferably, said intermediate essentially consists of a compound of formula IVa1 and/or Va1

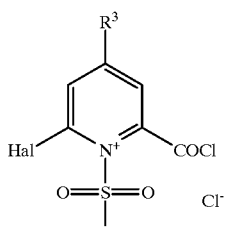

(IVa1)

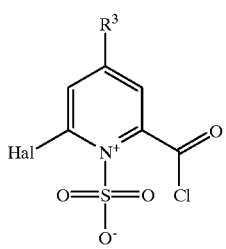

(Va1)

in the event that X represents $NR^2$, $R^1$ represents preferably a phenyl group being substituted by one or two halogen atoms and/or haloalkyl groups and $R^2$ represents preferably a hydrogen atom.

Another aspect of the present invention is a process for the preparation of a (hetero)aryloxyhetero-arylcarboxylic amide or ester of formula VI from the heteroarylcarboxylic amide or ester of formula I or a salt thereof obtained according to the present invention.

Further preferred embodiments of the process for preparation of the compounds of formula VI according to the present invention are a process wherein:

a heteroarylcarboxylic amide or ester of formula I or a salt thereof obtained according to the present invention is reacted with an aromatic or heteroaromatic hydroxyl compound of formula VII without further purification; or the salt of a heteroarylcarboxamide of formula I, wherein X represents NH, is treated with an alcohol of formula VII;

which comprises the following steps:

treating an ester of formula I, wherein X represents oxygen, in particular compound of formula IA,

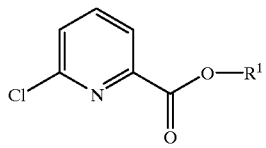

IA wherein $R^1$ represents an isopropyl group, with an alcohol of formula VII in the presence of a base, and treating the resulting ester of formula VI, in which X represents oxygen, in particular, the ester of formula VIA,

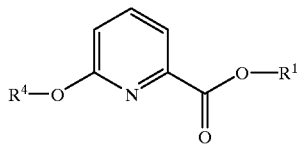

VIA wherein $R^4$ is as herebefore defined and $R^1$ represents an isopropyl group, with an amine of formula III in the presence of a base.

The esters of formulae I and VI (wherein X is oxygen) are partly known and partly novel. Accordingly, the invention relates to the novel esters of formulae I and IV, preferably wherein $R^1$ represents an isopropyl group, in particular, to the novel compounds of formulae IA and IVA.

Step (a) of the reaction according to the invention is generally carried out in the absence of solvent. The reaction is carried out at a temperature between ambient temperature and a temperature at which the reaction mixture is completely molten, preferably at an elevated temperature, preferably between about 100 and 160° C., in particular, between about 110 and 150° C. and most preferred, at about 135° C. As a rule, the reaction can be carried out under a reduced or elevated pressure, but preferably it is carried out at ambient pressure.

In a particularly preferred embodiment, 0.5 equivalents of the sulfuric acid (about 98% by weight) are added to the compound of formula II, preferably formula IIa, in particular nitrapyrin (NP), at temperatures between about 100 to 130° C., in particular about 110 to 125° C. Subsequently, the remaining amount of sulfuric acid (about 0.5 equivalents) is added at temperatures between about 110 and 140° C., in particular about 120 and 135° C. As a rule, the total amount of sulfuric acid is added to the compound of formula II over a period of about 2 to 6 hours. The reaction mixture is then preferably stirred at temperatures between 110 and 140° C.

In another particularly preferred embodiment of the process according to the invention, 1.1 to 1.4 equivalents, in particular about 1.3 equivalents, of the sulfuric acid (about 98% by weight) are added to the trichloromethylheteroaromatic compound of formula II, preferably formula IIa, in particular nitrapyrin (NP), at temperatures between 110 to 140° C., and, in particular at about 135° C. within about 1.5 to 4.0 hours. Subsequently, the reaction mixture is kept at this preferred temperature range for 2 to 4 hours.

Under these preferred reaction conditions, the reaction of step (a) is typically completed within about 3 to 8, in particular about 4 to 6 hours.

The resulting reaction mixture comprising a compound of formula IV and/or V or a tautomeric form thereof is preferably added to the amine or alcohol of formula III in a melted form or upon dilution with an inert solvent. Preferred solvents for dilution of the resulting intermediate of formula IV and/or V are highly polar solvents, for example, nitroalkanes such as nitroethane.

In a preferred embodiment, the melted mass comprising the intermediate of formula IV and/or V is transferred to the amine or alcohol of formula III.

Step (b) of the reaction according to the invention may be carried out in the absence or presence of a diluent which promotes the reaction or at least does not interfere with it. Preferred are apolar solvents, suitably being aliphatic hydrocarbons, such as hexane or cyclohexane, chlorinated hydrocarbons, such as dichloromethane or 1,2 dichloroethane, or aromatic hydrocarbons, such as toluene or xylene, or mixtures thereof. In the event that the intermediate formed in step (a) is reacted with an alcohol of formula III (X=oxygen), the reaction is typically carried out with an excess of said alcohol. Generally, the reaction with an amine of formula III (X=$NR^2$) is carried out in the presence of a base. Suitable bases are tertiary organic amines such as trialkylamines, in particular, triethylamine. The reaction is conducted at a temperature between ambient temperature and the reflux temperature of the reaction mixture, preferably at elevated temperatures between about 50 and 140° C., in particular, between about 60 and 120° C., and most preferably at about 80° C.

The reaction of step (b) can be carried out under a reduced or elevated pressure, but preferably, it is carried out at ambient pressure.

Under the preferred reaction conditions, the reaction is generally completed within about 0.5 to 5, and, in particular, about 1 to 4, hours.

Alternatively, the intermediate product obtained in step (a) may be treated with an alcohol of formula III which used in excess or in the presence of an inert diluent such as toluene, preferably with an aliphatic alcohol having 1 to 6, in particular 1 to 3, carbon atoms, and most preferably, with ethanol or isopropanol. The reaction of step (b) with an alcohol of formula III (X=oxygen) is generally conducted at a temperature between about 0° C. and +120° C., preferably at elevated temperatures between about 20 and 85° C., in particular, between about 40 and 70° C., and most preferably at about 65° C.

The resulting ester of formula I, wherein X represents oxygen, is preferably reacted with the amine of formula III in the presence of a base and an inert solvent which promotes the reaction or at least does not interfere with it. Preferred bases are metal alkoxides such as sodium methoxide or sodium ethoxide. Preferred are apolar solvents, particularly aliphatic hydrocarbons, such as hexane or cyclohexane, chlorinated hydrocarbons, such as dichloromethane or 1,2 dichloroethane, or aromatic hydrocarbons, such as toluene or xylene, or mixtures of any of these solvents.

When primary amines of formula III ($R^2$ represents a hydrogen atom) are used in the step for the transformation of an ester of formula I into an amide of formula I, the salts of formula I' are formed:

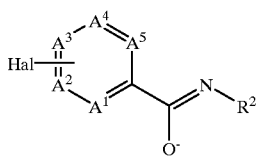

I' wherein $A^1$, $A^2$, $A^3$, $A^4$, $A^5$, Hal and $R^2$ are as hereinasbefore defined.

The obtained heteroarylcarboxylic amide or esters of formula I may be purified by standard procedures, as, for example, by crystallization or chromatography, in particular, by crystallization. However, since the compounds of formula I are obtained in high purity with the instant process, it is also possible to use the obtained product without further purification to prepare (hetero)aryloxyheteroarylcarboxylic amides or esters of formula VI.

In a preferred process of the invention a salt of formula I' obtained by the reaction of an ester of formula I with a primary amine of formula III ($R^2$=H) is directly converted into the compounds of formula VI without the use of any additional base.

In a particularly preferred embodiment of this invention, concentrated sulfuric acid (98% by weight) is added to the compound of formula II, in particular nitrapyrin (NP), over a period of about 2 to 4 hours at about 135° C. The resulting mixture is stirred for about 2 to 4 hours at about 135° C. The obtained melted mass which consists of a mixture of intermediate IVa and Va is added to a mixture of an aromatic hydrocarbon, in particular, toluene or xylene, and three (3) equivalents of an alcohol, in particular, ethanol or isopropanol, at a temperature below 60° C. The resulting reaction mixture is washed with water. A primary amine of formula III (0.9 to 1.2 eq.), preferably a halogenated aniline, in particular 4-fluoroaniline, and subsequently, sodium alkoxide, in particular, sodium methoxide in methanol, are added to this solution at a temperature of about 70 to 100° C. with stirring for about 1 to 3 hours. The solvents are then removed by distillation. The resulting sodium salt of formula I' is obtained in high yield as a mixture in the aromatic hydrocarbon and is used for the preparation of a compound of formula VI, preferably a N-(halophenyl) 2-(haloalkylphenoxy)-pyrid-6-ylinecarboxamide, in particular, N-(4-fluorophenyl) 2-(3-trifluoromethylphenoxy)-pyrid-6-ylinecarboxamide without further purification.

The compounds of formulae I or I' obtained according to the present invention are preferably treated with an alcohol of formula VII, preferably with an aromatic alcohol, in which $R^4$ represents a substituted phenyl group, in particular, a haloalkylphenyl group, most preferably with 3-trifluoromethylphenol, optionally in the presence of a base and an inert diluent.

Preferred bases are metal alkoxides or metal hydroxides such as sodium methoxide, sodium ethoxide, sodium hydroxide or potassium hydroxide. Preferred are apolar solvents or polar aprotic solvents, preferably aliphatic hydrocarbons, such as hexane or cyclohexane, chlorinated hydrocarbons, such as dichloromethane or 1,2 dichloroethane, or aromatic hydrocarbons, such as toluene or xylene, or amides such as dimethylformaide, N,N-dimethylacetamide or N-methylpyrrolidone, or mixtures of any of these solvents.

The reaction of the compound of formula I or I' with an alcohol of formula VII is generally carried out at a temperature between about 0° C. and +250° C., preferably at elevated temperatures between about 60 and 200° C., in particular, between about 140 and 180° C., and most preferably at about 160° C.

In a particularly preferred embodiment, the solution of the compound of formula I, in particular N-(4-fluorophenyl) 2-chloro-pyrid-6-ylinecarboxamide in the aromatic hydrocarbon obtained according to the invention is added to a mixture of the base, preferably a alkali hydroxide, in particular, potassium hydroxide, a polar aprotic solvent, in particular, N,N-dimethylacetamide, and the aromatic alcohol of formula VII, in particular, 3-hydroxybenzotrifluoride, at about 100 to 140° C. The resulting mixture is heated to temperatures between about 140 to 200° C. and the aromatic hydrocarbon and water formed during the reaction is distilled off. Subsequently, the mixture is stirred at elevated temperatures for about 1 to 4 hours. The solvent is removed by distillation under reduced pressure. The residue is diluted with an apolar solvent, in particular a mixture of aromatic and aliphatic hydrocarbons and washed with water or an aqueous alkali hydroxide. The aqueous phase is separated, removed and the organic phase is dried. The resulting crystals are collected by filtration, washed and dried at elevated temperatures and reduced pressure.

In another preferred embodiment of the present invention an ester of formula I (X=oxygen) is reacted with an alcohol of formula VII (step (c)) and the resulting ester of formula VI (X=oxygen) is subsequently treated with an amine of formula III (X=$NR^2$) (step (d)).

In a particularly preferred embodiment of this aspect of the present invention, the obtained melted mass which consists of a mixture of intermediate IVa and Va is added to 5 to −15 equivalents of an alcohol, in particular, isopropanol, at a temperature between about 20 and 85° C.

The resulting reaction mixture is diluted with an aromatic hydrocarbon and washed with water.

The resulting solution is added at temperatures from 120 to 160° C. to the phenolate which is obtained by treating an alcohol of formula VII (1.01 to 1.30, in particular, about 1.22 equivalents) and a solution of sodium alkoxide, in particular, sodium methoxide, in an alcohol (1.01 to 1.30, in particular, about 1.22 equivalents sodium alkoxide) in an aromatic hydrocarbon, in particular, xylene at 100–140° C. (step (c)).

Preferably, the excess of the remaining alcohol is removed by distillation before the ester of formula I is added to the phenolate. The reaction mixture is heated to about 140–160° C. and kept at this temperature for about 2–8 hours to complete the reaction. An amine of formula III (0.9 to 1.2 eqivalents), preferably a halogenated aniline, in particular, 4-fluoroaniline is added to the resulting reaction mixture at 120–150° C., in particular, at about 135° C., optionally followed by adding a sodium alkoxide, in particular, sodium methoxide solution (in catalytic amounts, preferably 0.05 to 0.20 equivalents, in particular, about 0.13 equivalents) in 10 to 60 minutes with simultaneous distillation of the alcohol used (step (d)). The reaction mixture is stirred for about 1 to 4 hours at 120 to 150° C., in particular, at about 135° C. to complete the reaction.

The novel process enables to carry out the production of heteroarylcarboxamides in technical scale and high yields using readily available reagents.

In order to facilitate a further understanding of the invention, the following illustrative examples are presented. The invention is not limited to the specific embodiments described or illustrated, but encompasses the full scope of the appended claims.

EXAMPLES

Example 1

Preparation of N-(4-fluorophenyl) 2-chloropyrid-6-ylcarboxamide

[$A^1$ is N, $A^2$ is Cl—C, $A^3$, $A^4$ and $A^5$ are CH, $R^1$ is 4-fluorophenyl, X is $NR^2$ and $R^2$ is H in the compound of formula I] Concentrated sulfuric acid (98% by weight, 98.1 g, 1 mol) is added to 2-chloro-6-trichloromethylpyridin (NP, 231 g, 1 mol) over a period of 4 hours. 50% of the sulfuric acid is added at 120° C., 38% at 125° C. and 12% at 130° C. The resulting mixture is stirred for 40 minutes at 130° C. A viscous melted mass is obtained consisting of >90% of a mixture of intermediate IVa1 and Va1 with $R^1$ being H and Hal being Cl. This mass is added to a mixture of 4-fluoroaniline (122.0 g 1.1 mol), triethylamine (202.0 g, 2 mol) and toluene (752 g) at temperatures between 20 and 100° C. within 45 minutes. The resulting reaction mixture is heated to temperatures between 80 and 120° C. and stirred for one hour. The mixture is treated with 500 ml of hydrochloric acid (7.5% by weight) at 80° C. and the phases are separated. The resulting solution of N-(4-fluorophenyl) 2-chloro-pyrid-6-ylinecarboxamide in toluene is used for the preparation of N-(4-fluorophenyl) 2-(3-trifluoromethylphenoxy)-pyrid-6-ylinecarboxamide without further purification.

Example 2

Preparation of N-(4-fluorophenyl) 2-chloro-pyrid-6-ylcarboxamide

[$A^1$ is N, $A^2$ is Cl—C, $A^3$, $A^4$ and $A^5$ are CH, $R^1$ is 4-fluorophenyl, X is $NR^2$ and $R^2$ is H in the compound of formula I] Concentrated sulfuric acid (98% by weight, 127.5 g, 1.3 mol) is added to 2-chloro-6-trichloromethylpyridin (NP, 231 g, 1 mol) over a period of three hours at 135° C. The resulting mixture is stirred for three hours at 135° C. A viscous melted mass is obtained consisting of a mixture of intermediate IVa1 and Va1 with $R^1$ being H and Hal being Cl, corresponding to a yield of >95% based on NP. This intermediate product shows a strong infrared band at 1770cm−1 indicating a carbonylchloride group. $^{13}$C-NNR (TMS/nitromethane-$d_3$): δ=130.2 (CH-5), 135.3 (CH-3), 143.7 (C-2), 151.4 (CCl-6), 151.5 (CH-4), 164.1 (C=O) ppm. The mass is added to a mixture of 4-fluoroaniline (166.4 g 1.5 mol), triethylamine (202.0 g, 2 mol) and toluene (752 g) at temperatures between 20 and 80° C. over a period of 45 minutes. The resulting reaction mixture is heated to temperatures between 80 and 100° C. and stirred for one hour. The mixture is treated with 500 ml of hydrochloric acid (1.0% by weight) at 80° C. and the phases are separated. The resulting solution of N-(4-fluorophenyl) 2-chloro-pyrid-6-ylinecarboxamide in toluene is used for the preparation of N-(4-fluorophenyl) 2-(3-trifluoromethylphenoxy)-pyrid-6-ylinecarboxamide without further purification.

Example 3

Preparation of N-(4-fluorophenyl) 2-chloro-pyrid-6-ylcarboxamide

[$A^1$ is N, $A^2$ is Cl—C, $A^3$, $A^4$ and $A^5$ are CH, $R^1$ is 4-fluorophenyl, X is $NR^2$ and $R^2$ is H in the compound of formula I] Concentrated sulfuric acid (98% by weight, 310 g, 1 eq.) is added to 2-chloro-6-trichloromethylpyridin (NP, 730 g, 1 eq.) over a period of 6 hours. 50% of the sulfuric acid are added at 120° C., 35% at 125° C. and 15% at 130° C. The resulting mixture is stirred for 30 minutes at 130° C.

The viscous melted mass obtained is diluted with nitroethane (500 ml) at temperatures between 80 to 90° C.

The resulting solution is added to a mixture of 4-fluoroaniline (122.0 g 1.1 eq.), triethylamine (202.0 g, 2 eq.) and nitroethane (250 ml) at temperatures between 50 and 80° C. Subsequently, the mixture is heated to 90° C. with stirring for one hour. Hydrochloric acid (10%, 700 ml) is added at 70° C. and the aqueous phase is separated. The product is obtained as a solution in nitromethane, which is used for the preparation of N-(4-fluorophenyl) 2-(3-trifluoromethylphenoxy)-pyrid-6-ylinecarboxamide without further purification.

Example 4

Preparation of the sodium salt of N-(4-fluorophenyl) 2-chloro-pyrid-6-ylcarboxamide

[$A^1$ is N, $A^2$ is Cl—C, $A^3$, $A^4$ and $A^5$ are CH, $R^1$ is 4-fluorophenyl, X is $NR^2$ and $R^2$ is H in the compound of formula I] Concentrated sulfuric acid (98% by weight, 127.5 g, 1.3 mol) is added to 2-chloro-6-trichloromethylpyridin (NP, 231 g, 1 mol) over a period of 3 hours at 135° C. The resulting mixture is stirred for 3 hours at 135° C. A viscous melted mass is obtained consisting of a mixture of intermediate IVa1 and Va1 with $R^1$ being H and Hal being Cl, corresponding to a yield of >95% based on NP. The mass is dosed to a mixture of toluene (500 ml) and 3 equivalents of ethanol at a temperature below 60° C. The resulting reaction mixture is washed with water twice. The obtained solution contains 30% w/v ethyl 2-chloropyrid-6-ylcarboxylate in toluene which corresponds to a yield of 90% based on NP. 4-Fluoroaniline (122.0 g 1.1 eq.) and subsequently sodium methoxide in methanol (1.6 eq; 30% w/v) are added to this solution at a temperature of 85° C. with stirring for two hours. The solvents are removed by distillation. The resulting sodium salt is obtained in 95% yield as a mixture in toluene and is used for the preparation of N-(4-fluorophenyl) 2-(3-trifluoromethylphenoxy)-pyrid-6-ylinecarboxamide without further purification (Example 8).

Example 5

Preparation of N-(2,4-difluorophenyl) 2-chloropyrid-3-ylcarboxamide

[$A^2$ is N, $A^1$ is Cl—C, $A^3$, $A^4$ and $A^5$ are CH, $R^1$ is 2,4-difluorophenyl, X is $NR^2$ and $R^2$ is H in the compound of formula I] Analogous to the process described in Example 1,2-chloro-3-trichloromethylpyridin (231 g, 1 mol) is treated with concentrated sulfuric acid (98% by weight, 98.1 g, 1 mol) and subsequently reacted with 2,4-difluoroaniline (142.0 g 1.1 mol) in the presence of trietylamine and toluene. The resulting solution of N-(2,4-difluorophenyl) 2-chloropyrid-3-ylcarboxamide in toluene is used for the preparation of N-(2,4-difluorophenyl) 2-(3-trifluoromethylphenoxy)-pyrid-3-ylcarboxamide without further purification.

Example 6

Preparation of isopropyl 2-chloropyrid-6-ylcarboxylate

[$A^1$ is N, $A^2$ is Cl—C, $A^3$, $A^4$ and $A^5$ are CH, X is O and $R^1$ isopropyl in the compound of formula I] Concentrated sulfuric acid (98% by weight, 510.2 g, 5.2 mol) is added to 2-chloro-6-trichloromethylpyridine (NP, 924 g, 4 mol) over a period of three hours at 135° C. The resulting mixture is stirred for three hours at 135° C. A viscous melted mass is obtained consisting of a mixture of intermediate IVa1 and Va1 with $R^1$ being H and Hal being Cl, corresponding to an almost quantitative yield based on NP. The mass is added to isopropanol (2145 g) over a period of 30 minutes starting at ambient temperature which is raised to 60–65° C. Remaining isopropanol is removed by distillation under reduced pressure in three hours. The resulting product mixture is added to a mixture of xylene (1800 g) and water (1500 g). Upon heating to 50° C. the organic phase is separated and washed with water (1000 g). The obtained organic phase is dried and concentrated by distillation of xylene under reduced pressure (250 mbar). The resulting product (2070 g) contains 34.1 wt % of isopropyl 2-chloropyrid-6-ylcarboxylate in xylene which corresponds to a yield of 8.4% based on NP and is used for the preparation of N-4-fluorophenyl) 2-(3-trifluoromethylphenoxy)-pyrid-6-ylinecarboxamide without further purification (Examples 9 and 10).

Example 7

Preparation of N-(4-fluorophenyl) 2-(3-trifluoromethylphenoxy)-pyrid-6-ylinecarboxamide

[$A^1$ is N⁻, $A^2$ is C, $A^3$, $A^4$ and $A^5$ are CH, $R^1$ is 4-fluorophenyl, X is $NR^2$, $R^2$ is H and $R^4$—O is 3-trifluoromethylphenoxy attached to $A^2$ in the compound of formula VI] The solution of N-(4-fluorophenyl) 2-chloro-pyrid-6-ylinecarboxanide (13.5% 0.226 mol) in toluene obtained according to Example 2 is added to a mixture of potassium hydroxide (19.8 g, 0.300 mol), N,N-dimethylacetamide (200 ml)and 3-hydroxybenzotrifluoride (0.291 mol) at 120° C. with stirring. The resulting mixture is heated to 160° C. and toluene and water formed during the reaction is removed by distillation. Subsequently, the mixture is stirred at 160° C. for two hours. The solvent is removed by distillation under reduced pressure (30 mbar) at 140° C. The residue is diluted wit xylene (150 ml) and isooctane (550 ml) and washed with water at 80° C. The aqueous phase is separated and removed, and the organic phase is dried, diluted with isooctane (80 ml) and cooled down to 10° C. over a period of four hours. The resulting crystals are collected by filtration and washed with isooctane and dried at 45° C. and 100 mbar. N-(4-fluorophenyl) 2-($^3$-trifluoromethylphenoxy)-pyrid-6-ylinecarboxamide (73.2 g) is obtained as a white solid with a purity of 97% representing an overall yield of 83.5% based on the amide obtained in Example 2.

Using the solution of N-(2,4-difluorophenyl) 2-chloro-pyrid-3-ylcarboxamide in toluene obtained according to Example 3 N-(2,4-difluorophenyl) 2-(3-trifluoromethyl-phenoxy)-pyrid-3-ylinecarboxamide is analogously obtained.

Example 8

Preparation of N-(4-fluorophenyl) 2-(3-trifluoromethylphenoxy)-pyrid-6-ylinecarboxamide

[$A^1$ is N, $A^2$ is C, $A^3$, $A^4$ and $A^5$ are CH, $R^1$ is 4-fluorophenyl, X is $NR^2$, $R^2$ is H and $R^4$—O is 3-trifluoromethylphenoxy attached to $A^2$ in the compound of formula VI] 3-Hydroxybenzotrifluoride (0.291 mol) is added to the mixture of the sodium salt of N-(4-fluorophenyl) 2-chloro-pyrid-6-ylinecarboxamide (30%, 0.226 mol) and toluene obtained according to Example 4, subsequently N,N-dimethylacetamide (200 ml)and is added at 80° C. with stirring. Toluene is distilled off under reduced pressure. Subsequently, the mixture is stirred at 160° C. for two hours. The solvent is removed by distillation under reduced pressure (30 mbar) at 140° C. The residue is diluted with xylene (150 ml) and isooctane (550 ml) and washed with water at 80° C. The aqueous phase is separated and removed, and the organic phase is dried, diluted with isooctane (80 ml) and cooled down to 10° C. over a period of four hours. The resulting crystals are collected by filtration and washed with isooctane and dried at 45° C. and 100 mbar. N-(4-fluorophenyl)-2-(3-trifluoromethylphenoxy)-pyrid-6-ylinecarboxamide (73.2 g) is obtained as a white solid with a purity of 97% representing an overall yield of 70.0% based on NP.

Example 9

Preparation of isopropyl 2-(3-trifluoromethylphenoxy)-pyrid-6-ylinecarbonate

[$A^1$ is N⁻$A^2$ is C, $A^{3,}$ $A^4$ and $A^5$ are CH, $R^1$ is isopropyl, X is O, $R^2$ is H and $R^2$ and $R^4$—O is 3-trifluoromethylphenoxy attached to $A^2$ in the compound of formula VI] A 30%wt solution of sodium methoxide in methanol (212.5 g; .22 equivalents NaOMe) is added over 1 hour to a solution of 3-hydroxybenzotrifluoride (194.5 g; 1.24 equivalents) in xylene (856 g; 8.31 equivalents) at 120–110° C., with simultaneous distillation of methanol. The resulting phenolate mixture is slowly heated to 140° C. to remove remaining methanol. A solution of isopropyl 2-chloro-pyrid-6-ylcarboxylate in xylene (Example 6; 194.5 g CPAPE; 0.97 mol) is added at 140° C. to the phenolate mixture in 30 minutes, followed by further heating and distillation of xylene to get a batch temperature of 150–155° C. which is kept for 4–6 hours to complete the reaction. The resulting reaction mixture is cooled to 135° C. and directly used in Example 10.

Example 10

Preparation of N-(4-fluorophenyl) 2-(3-trifluoromethylphenoxy)-pyrid-6-ylinecarboxamide

[A is N, $A^2$ is C, $A^3$, $A^4$ and $A^5$ are CH, $R^1$ is 4-fluorophenyl, X is $NR^2$, $R^2$ is H and $R^4$—O is 3-trifluoromethylphenoxy attached to $A^2$ in the compound of formula VI] 4-Fluoroaniline (111.1 g; 1.03 equivalents) is added to the reaction mixture from Example 9 at 135° C., followed by dosing in 30% wt sodium methoxide solution (24.3 g; 0.13 equivalents) in 30 minutes with simultaneous distillation of methanol. The reaction mixture is stirred for two hours at 135° C. to complete the reaction. The reaction mixture is then added to a mixture of isooctane (1046 g) and water (500 g) at 70° C., resulting in a final temperature of 80° C. The aqueous phase is separated, removed, and the organic phase is washed with water (250 g) at 80° C. The resulting product solution is dried azeotropically under Dean-Stark conditions to a final batch temperature of 105–110° C. The product solution is cooled to 5° C. in five hours, including seeding at 68° C. The crystallised product is filtered, washed with isooctane (410 g) and dried at 45° C. and 100 mbar. Trifluoromethylphenoxy)-pyrid-6-ylinecarboxamide (316.5 g) is obtained as a white solid with a purity of 99.3%, representing an overall yield of 75.8% based on NP.

Comparison Example

Treatment of NP with Sulfuric Acid According to U.S. Pat. No. 3,317,549

A mixture of 20 g nitrapyrin (NP) and 70 g (7.9 equivalents) concentrated sulfuric acid is heated to 125–130° C. for 60 minutes. The mixture is cooled and diluted with 8 g of ice water. Subsequently, any solid material is filtered off and 71 ml of water are added. Upon crystallization and drying, 12.5 g of a white solid is obtained which consists of 92% of 6-chloropyrid-2-ylcarboxylic acid. This product is treated with thionylchloride, then with 4-fluoroaniline and subsequently with 3-hydroxybenzotrifluoride as disclosed by EP 0 447 004 A to obtain N-(4-fluorophenyl) 2-(3-trifluoromethylphenoxy)-pyrid-6-ylinecarboxamide (18,6 g)representing an overall yield of 65%.

What is claimed is:

1. A process for the preparation of a (hetero)aryloxyheteroarylcarboxylic amide or ester of formula VI

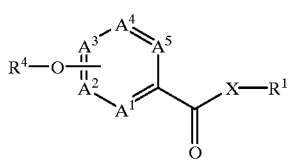

VI wherein
one of the groups $A^1$, $A^2$, $A^3$, $A^4$ and $A^1$ represent a nitrogen atom and the other groups each independently represent $CR^3$,
Hal represents a halogen atom,
X represents O or $NR^2$,
$R^1$ represents an optionally substituted alkyl, aryl, heteroaryl or cycloalkyl group,
$R^2$ represents a hydrogen atom or an alkyl group, or
$R^1$ and $R^2$ together with the interjacent ring form a heterocyclic group, and
$R^3$ each independently represent a hydrogen atom or an alkyl group, and $R^4$ represents an optionally substituted aryl or heteroaryl group, which process comprises preparing the heteroarylcarboxylic amide or ester of formula I or a salt thereof,

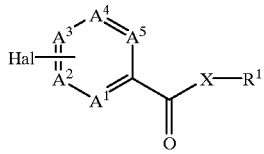

I wherein Hal, $A^1$ to $A^5$, and $R^1$ are as defined above, from a trichloromethyl-heteroaromatic compound of formula II

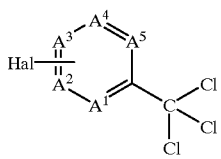

II and reacting the compound of formula I with an aromatic or heteroaromatic hydroxyl compound of formula VII,

  VII wherein $R^4$ is as hereinbefore defined, optionally in the presence of a base.

2. A process according to claim 1, in which a heteroarylcarboxylic amide or ester of formula I or a salt thereof is reacted with an aromatic or heteroaromatic hydroxyl compound of formula VII without further purification.

3. A process according to claim 1 or 2 for the preparation of a compound of formula VI, wherein X represents NH, in which the salt of a heteroarylcarboxamide of formula I is treated with an alcohol of formula VII.

4. A process according to claim 1 or 2 for the preparation of a compound of formula VI, wherein X represents NH, which comprises the steps of treating an ester of formula I wherein X represents O, with an alcohol of formula VII in the presence of a base, and treating the resulting ester of formula VI, with an amine of formula III in the presence of a base.

5. A process according to claim 4 wherein the compound of formula IA,

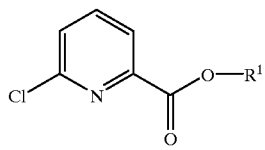

IA wherein $R^1$ represents an isopropyl group, is treated with an alcohol of formula VII.

6. The compound of formula IA,

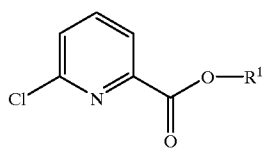

IA wherein $R^1$ represents an isopropyl group.

7. A process for the preparation of a (hetero)aryloxyheteroarylcarboxylic amide or ester of formula VI

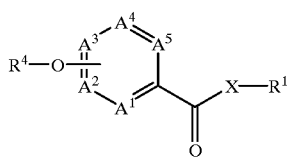

VI wherein
one of the groups $A^1$, $A^2$, $A^3$, $A^4$ and $A^5$ represent a nitrogen atom and the other groups each independently represent $CR^3$,
Hal represents a halogen atom,
X represents $NR^2$,
$R^1$ represents an optionally substituted alkyl, aryl, heteroaryl or cycloalkyl group,
$R^2$ represents a hydrogen atom or an alkyl group, or
$R^1$ and $R^2$ together with the interjacent ring form a heterocyclic group, and
$R^3$ each independently represent a hydrogen atom or an alkyl group, and $R^4$ represents an optionally substituted aryl or heteroaryl group, which process comprises preparing the heteroarylcarboxylic amide or ester of formula I or a salt thereof,

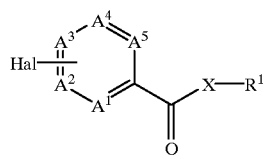

wherein Hal, $A^1$ to $A^5$, and are as defined above and X is O or $NR^2$, from a trichloromethyl-heteroaromatic compound of formula II

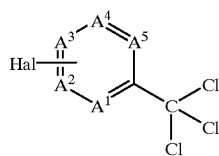

and reacting the compound of formula I with an aromatic or hetemaromatic hydroxyl compound of formula VII, $R^4$—OH   VII wherein $R^4$ is as hereinbefore defined, optionally in the presence of a base.

8. A process according to claim 7, in which a heteroarylcarboxylic amide or ester of formula I or a salt thereof is reacted with an aromatic or heteroaromatic hydroxyl compound of formula VII without further purification.

9. A process according to claim 7 or 8 for the preparation of a compound of formula VI, in which the salt of a heteroarylcarboxamide of formula I is treated with an alcohol of formula VII.

10. A process according to claim 7 or 8 for the preparation of a compound of formula VI, which comprises the steps of treating an ester of formula I, wherein X represents O, with an alcohol of formula VII in the presence of a base, and treating the resulting ester of formula VI, with an amine of formula III in the presence of a base.

11. A process according to claim 10 wherein the compound of formula IA,

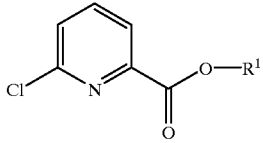

wherein $R^1$ represents an isopropyl group, is treated with an alcohol of formula VII.

12. The compound of formula VIA

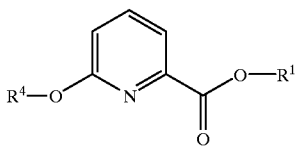

wherein $R^4$ represents an optionally substituted aryl or heteroaryl group and $R^1$ represents an isopropyl group.

* * * * *